(12) United States Patent
Madry et al.

(10) Patent No.: US 7,252,982 B2
(45) Date of Patent: Aug. 7, 2007

(54) TISSUE ENGINEERING ENHANCED BY THE TRANSFER OF A GROWTH FACTOR GENE

(75) Inventors: Henning Madry, Homburg (DE); Gordana Vunjak-Novakovic, Belmont, MA (US); Stephen B. Trippel, Auburndale, MA (US); Lisa E. Freed, Belmont, MA (US); Robert Langer, Newton, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 09/809,456

(22) Filed: Mar. 15, 2001

(65) Prior Publication Data

US 2002/0177224 A1 Nov. 28, 2002

(51) Int. Cl.
 *C12N 11/08* (2006.01)
 *C12N 5/06* (2006.01)
 *C12N 5/00* (2006.01)
 *C12N 5/02* (2006.01)
 *C12M 1/00* (2006.01)

(52) U.S. Cl. .................. 435/180; 435/283.1; 435/347; 435/373

(58) Field of Classification Search ................ 435/180, 435/283.1, 347, 373, 382
See application file for complete search history.

(56) References Cited

U.S. PATENT DOCUMENTS

| 5,766,585 | A |   | 6/1998 | Evans et al. |         |
|-----------|---|---|--------|--------------|---------|
| 5,785,964 | A | * | 7/1998 | Naughton et al. |      |
| 5,858,355 | A |   | 1/1999 | Glorioso et al. |      |
| 5,891,455 | A |   | 4/1999 | Sittinger et al. |     |
| 5,932,459 | A | * | 8/1999 | Sittinger et al. | 435/180 |
| 6,077,987 | A | * | 6/2000 | Breitbart et al. |     |

OTHER PUBLICATIONS

Alila, "Expression of Biologically active human insulin-like growth factor-I following intramuscular injection of a formulated plasmid in rats," *Hum Gene Ther* 8:1785-95, 1997.
Baragi, "Transplantation of transduced chondrocytes protects articular cartilage from interleukin 1-induced extracellular matrix degradation," *J Clin Invest* 96:2454-60, 1995.
Barton-Davis, et al., "Viral mediated expression of insulin-like growth factor I blocks the aging-related loss of skeletal muscle function," *Proc Natl Acad Sci U S A* 95:15603-7, 1998.
Bonadio, et al., "Localized, direct plasmid gene delivery in vivo: prolonged therapy results in reproducible tissue regeneration," *Nat Med* 5:753-759, 1999.
Buckwalter, et al., "Articular cartilage repair and transplantation.," *Arthritis Rheum* 41:1331-1342, 1998.
Doherty, et al., "Resurfacing of articular cartilage explants with genetically-modified human chondrocytes in vitro," *Osteoarthritis Cartilage* 6:153-9, 1998.
Evans, et al., "Possible orthopaedic applications of gene therapy," *J Bone Joint Surg Am* 77A:1103-14, 1995.
Eming, et al., "Targeted expression of insulin-like growth factor to human keratinocytes: modification of the autocrine control of keratinocyte proliferation," *J Invest Dermatol* 107:113-120, 1996.
Farndale, "Improved Quantification of Sulphated Glycosaminoglycans by Use of Dimethylmethylene Blue," *Biochem Biophys Acta*, 883: 173-177, 1986.
Frank, et al., "Strearming Potentials: A Sensitive Index of Enzymatic Degradation in Articular Cartilage", *Journal of Orthopaedic Research*, 5(4): 497-508, 1987.
Frank, et al., "Cartilage Electromechanics—II. A Continuum Model of Cartilage Electrokinetics and Correlation with Experiments," *J. Biomech*, 20: 629-639, 1987.
Freed, et al., "Tissue engineering of cartilage in space," *Proc Natl Acad Sci U S A* 94:13885-13890, 1997.
Freed, "Chondrogenesis in a cell-polymer-bioreactor system," *Exp Cell Res* 240:58-65, 1998.
Freed, et al., "Frontiers in Tissue Engineering", Clinical Orthopaedics and Related Research, 367S: S46-S58.
Ikeda, "Adenovirus mediated gene delivery to the joints of guinea pigs," *J Rheumatol* 25:1666-73, 1998.
Jansen, "Sequence of cDNA Encoding Human Insulin-Like Growth Factor I Precursor," *Nature*, 306: 609-611, 1983.
Kang, "Ex vivo gene transfer to chondrocytes in full-thickness articular cartilage defects: a feasibility study," *Osteoarthritis Cartilage* 5:139-43, 1997.
Kim, et al., "Fluorometric assay of DNA in cartilage explants using Hoechst 33258," *Anal Biochem* 174:168-76, 1988.
Kitamura, et al., "Creation of an In vivo cytosensor using engineered mesangial cells. Automatic sensing of glomerular inflammation controls transgene activity," *J Clin Invest* 100:1394-9, 1997.
Langer, et al., "Tissue Engineering," *Science* 260:920-926, 1993.
Lauffenburger, et al., "The Matrix Delivers", *Nature Medicine*, 5(7): 733-734, 1999.
Madry, et al., "Efficient lipid-mediated gene transfer to articular chondrocytes," *Gene Ther* 7:286-291, 2000.
Mulligan, "The basic science of gene therapy," *Science* 260:926-932, 1993.
Nixon, et al., "Enhanced repair of extensive articular defects by insulin-like growth factor-I-laden fibrin composites," *J Orthop Res* 17:475-487, 1999.

(Continued)

Primary Examiner—James Ketter
Assistant Examiner—Konstantina Katcheves
(74) Attorney, Agent, or Firm—Choate, Hall & Stewart LLP; Valarie B. Rosen (57) ABSTRACT

Tissue engineered constructs including a matrix and cells transfected with a gene for a growth factor. The constructs may be implanted into a tissue site, where the growth factor gene enhances a metabolic function furthering integration of the construct in the tissue site. If the matrix is biodegradable, the metabolic result may include resorption of the matrix and replacement with tissue synthesized at least in part by the transfected cells.

11 Claims, 4 Drawing Sheets
(2 of 4 Drawing Sheet(s) Filed in Color)

OTHER PUBLICATIONS

O'Driscoll, "The healing and regeneration of articular cartilage," *J Bone Joint Surg Am* 80A:1795-12, 1998.

Olney, et al., "Production and hormonal regulation of insulin-like growth factor binding proteins in bovine chondrocytes," *Endocrinology* 133:563-570, 1993.

Peppas, et al., "New Challenges in Biometerials", *Science*, 263: 1715-1720, 1994.

Powell, "Tissue-engineered human bioartificial muscles expressing a foregin recombinant protein for gene therapy," *Hum Gene Ther*, 10:565-577, 1999.

Saltzman, "Delivering Tissue Regeneration", *Nature Biotechnology*, 17: 534-535, 1999.

Smith, "Genetic enhancement of matrix synthesis by articular chondrocytes," *J Rheumatol* 43:1156-64, 2000.

Trippel, et al., "Characterization of a Specific Somatomedin-c Receptor on Isolated Bovine Growth Plate Chondrocytes," *Endocrinology*, 112: 2128-2136, 1983.

Trippel, "Effect of somatomedin-C/insulin-like growth factor I and growth hormone on cultured growth plate and articular chondrocytes," *Pediatr Res* 25:76-82, 1989.

Trippel, "Growth factor actions on articular cartilage," *J Rheumatol Suppl* 43:129-32, 1995.

Trippel, "Growth factors as therapeutic agents," *Instr Course Lect* 46:473-6, 1997.

Vandenburgh, "Tissue-engineered skeletal muscle organoids for reversible gene therapy," *Hum Gene Ther* 7:2195-2200, 1996.

Vandenburgh, et al., "Attenuation of Skeletal Muscle Wasting with Recombinant Human Growth Hormone Secreted from a Tissue-Engineered Bioartificial Muscle", *Human Gene Therapy*, 9:2555-2564, 1998.

Von der Mark, et al., "Relationship Between Cell Shape and Type of Collagen Synthesised as Chondrocytes Lose Their Cartilage Phenotype in Culture", *Nature*, 267: 531-532, 1977.

Vunjak-Novakovic, "Dynamic cell seeding of polymer scaffolds for cartilage tissue engineering," *Biotechnol Prog* 14:193-202, 1998.

Woessner, "The Determination of Hydroxyproline in Tissue and Protein Samples Containing Small Proportions of this Imino Acid," *Arch Biochem Biophys*, 93: 440-447, 1961.

Schnabel, et al., Dedifferentiation-associated changes in morphology and gene expression in primary human articular chondrocytes in cell culture, *Osteoarthritis and Cartilage* (2002) 10 62-70.

\* cited by examiner

TISSUE ENGINEERING ENHANCED BY THE TRANSFER OF A GROWTH FACTOR GENE

This invention was partially made with Government support under grants NAG 9-836 and NCC 8-174 from the National Aeronautical and Space Administration and AR 31068 and AR 45749 from the National Institutes of Health. The United States Government has certain rights in this invention. This invention was also partially made with assistance from Leopoldina Fellowship Grant BMBF-LPD 9801-10.

FIELD OF THE INVENTION

This invention pertains to the use of genetically enhanced cells for tissue engineering and, more particularly, to the use of cells transfected with genes for growth factors.

BACKGROUND OF THE INVENTION

Physiological tissues and organs have adopted a variety of mechanisms for healing wounds and defects. For example, a cut in the skin may be healed by the formation of fibrous tissue, or scar, that connects the edges of the wound and protects interior tissues from the environment. Scar does not have the same mechanical or biological properties as undamaged skin. This healing mechanism, called repair, does not replace the structure or function of the original, undamaged tissue.

In contrast, organs such as liver have the ability to regenerate, replacing the wounded tissue with new, fully functional tissue having the same biological and mechanical properties as the original. Many tissues that typically heal by repair also have the ability to heal by regeneration. For example, small wounds such as paper cuts in the skin typically heal by regeneration, while larger wounds such as burns heal by formation of scar tissue. Furthermore, there are some tissues that do not properly heal at all on their own. To remedy defects and injuries in such tissue, physicians frequently attempt to artificially promote, repair or regeneration in such tissues.

In one example, articular cartilage lesions do not heal properly if left untreated, yet effective treatment methods remain an unsolved problem (Buckwalter, (1998) "Articular cartilage repair and transplantation." *Arthritis. Rheum.* 41: 1331–1342). Tissue engineering (Langer, et al. (1993) "Tissue Engineering." *Science* 260: 920–6) and gene therapy (Mulligan, (1993) "The basic science of gene therapy." *Science* 260: 926–932) are two novel approaches to regenerate articular cartilage (see Evans, et al. (1999), "Genetically augmented tissue engineering of the musculoskeletal system" *Clin. Orthop.* 367 Suppl.:S410–418). Three-dimensional, functional cartilaginous tissue can be generated in bioreactors using isolated chondrocytes cultured on biodegradable scaffolds (Freed, (1997) "Tissue engineering of cartilage in space." *Proc. Natl. Acad. Sci. U S A* 94: 13885–90; Vunjak-Novakovic, et al, (1999) "Bioreactor cultivation conditions modulate the composition and mechanical properties of tissue engineered cartilage." *J Orthop. Res.* 17: 130–138). The functional properties of the engineered constructs develop over the time of cultivation and come into the range of values measured for native articular cartilage only after several months of culture (Freed, 1997). Moreover, adult articular chondrocytes are problematic as a cell source for a clinical scenario of therapeutic tissue engineering due to their very low mitotic activity. However, isolated articular chondrocytes can be genetically modified (Baragi, et al. (1995) "Transplantation of transduced chondrocytes protects articular cartilage from interleukin 1-induced extracellular matrix degradation." *J. Clin. Invest.* 96: 2454–60; Kang et al., (1997) "Ex vivo gene transfer to chondrocytes in full-thickness articular cartilage defects: A feasibility study." *Osteoarthritis Cartilage* 5: 139–43; Doherty et al., (1998) "Resurfacing of articular cartilage explants with genetically-modified human chondrocytes in vitro." *Osteoarthritis Cartilage* 6: 153–9; Madry, et al. (2000) "Efficient lipid-mediated gene transfer to articular chondrocytes." *Gene Ther.* 7: 286–91) to express potentially beneficial genes (Doherty, 1998; Madry, 2000; Smith, et al. (2000) "Genetic enhancement of matrix synthesis by articular chondrocytes." *J. Rheumatol.* 43: 1156–64). Insulin-like growth factor-I (IGF-I), a 7.6 kDa polypeptide growth factor, is a candidate gene to improve tissue engineering of cartilage, as it stimulates chondrocyte mitotic activity, increases proteoglycan and type-II collagen synthesis in vitro (Trippel, et al. (1997) "Growth factors as therapeutic agents." *Instr. Course. Lect.* 46: 473–6) and enhances articular cartilage repair in vivo (Nixon, et al. (1999) "Enhanced repair of extensive articular defects by insulin-like growth factor-I-laden fibrin composites." *J. Orthop. Res.* 17: 475–87). The application of chondrocytes that were genetically modified ex vivo to articular cartilage defects (Kang, 1997) is complicated due to technical challenges, such as the problem of cell loss after transplantation (O'Driscoll, et al (1998), "The healing and regeneration of articular cartilage." *J. Bone Joint Surg. Am.* 80: 1795–12). Moreover, direct gene transfer into cartilage is difficult due to the dense matrix in which the chondrocytes are embedded (Ikeda, et al. (1998). "Adenovirus mediated gene delivery to the joints of guinea pigs." *J. Rheumatol.* 25: 1666–73).

Gene transfer has been successfully applied to the tissue engineering of bioartificial muscle expressing a therapeutic protein (Powell, et al. (1999) "Tissue-engineered human bioartificial muscles expressing a foreign recombinant protein for gene therapy." *Hum. Gene Ther.* 10: 565–77) or to achieve the sustained release of plasmid DNA when associated with a biodegradable carrier in vivo (Bonadio, et al. (1999) "Localized, direct plasmid gene delivery in vivo: prolonged therapy results in reproducible tissue regeneration." *Nat. Med.* 5: 753–9). Recent studies have demonstrated that isolated articular chondrocytes can be genetically modified (Baragi, 1995; Kang, 1997; Doherty, 1998; Madry, 2000) to express potentially beneficial genes (Baragi, 1995; Smith, 2000). Insulin-like growth factor-I (IGF-I), a 7.6 kDa polypeptide growth factor, stimulates chondrocyte mitotic activity, increases proteoglycan and type-II collagen synthesis in vitro (Trippel, 1997) and enhances articular cartilage repair in vivo (Nixon, 1999).

One approach to tissue engineering is to promote regeneration of lost or damaged tissue by providing materials that facilitate regenerative processes. For example, cells may be implanted into a wound site and allowed to generate extracellular matrix and other molecules that ordinarily form part of the normal tissue. Cells may also be taken from a patient or other source and utilized to synthesize tissue in vitro, following which the naturally synthesized tissue is transferred to the wound site.

Alternatively, a wound site may be implanted with a synthetic extracellular matrix that initially promotes migration of cells from the edges of a wound and later promotes normal metabolic and synthetic activity in the cells, enabling them to produce new tissue that will eventually replace the implanted matrix. Alternatively, these matrices may be coated with growth factors or other regulators designed to up-regulate certain metabolic activities in cells. They may also be coated with genetic material, which is then taken up into the cells where they control the production of desired proteins. In vitro cell cultures are also frequently transfected with DNA for specific growth factors or regulators. The DNA may be transferred directly into the cells or placed in the cell culture, where the cells uptake the genetic material through their membranes. However, the efficiency of cellular uptake of DNA varies, and some cells, such as chondrocytes, have not been demonstrated to uptake DNA immobilized on a cellular scaffold. Thus, it is desirable to employ more reliable transfection techniques for cells that are seeded in matrices for tissue engineered implants. It is hypothesized that the utilization of genetically engineered cells will improve the functionality of engineered tissue, while the incorporation of genetically engineered cells will improve cell delivery to the implantation site.

SUMMARY OF THE INVENTION

In one aspect, the invention is a method of assembling a tissue engineered construct. The method comprises transfecting a plurality of mammalian cells with a gene for a growth factor. The method may further comprise culturing the cells until they synthesize a desired amount of extracellular matrix or seeding the cells onto a biocompatible matrix. The matrix may comprise a synthetic or a nonsynthetic material. For example, the matrix may comprise poly(glycolic acid), collagen-glycosaminoglycan, collagen, poly(lactic acid), poly(lactic-co-glycolic acid, poly(anhydride), poly(hydroxy acid), poly(orthoester), poly(propylfumerate), polysaccharide, polypyrrole, polyaniline, polythiophene, polystyrene, polyester, polyurethane, polyurea, poly(ethylene vinyl acetate), polypropylene, polymethacrylate, polyethylene, poly(ethylene oxide), poly(carbonate), or any combination thereof. The cells may be human cells, for example, chondrocytes, hepatocytes, Islet cells, nerve cells, muscle cells, bone-forming cells, fibroblasts, endothelial cells, stem cells, connective tissue stem cells, mesodermal stem cells and epithelial cells. A cell attachment facilitator may be attached to the matrix. The facilitator may comprise an integrin, cell adhesion sequence, basement membrane component, agar, or collagen. In addition, a cell metabolism regulator may be added to the matrix. The growth factor may be a protein, for example, TGF-β, acidic fibroblast growth factor, basic fibroblast growth factor, epidermal growth factor, IGF-I or II, vascular endothelial-derived growth factor, bone morphogenetic proteins, platelet-derived growth factor, heparin-binding growth factor, hematopoetic growth factor, or peptide growth factor. The transfection may be accomplished with or without a viral vector. For example, transfection may be accomplished with a lipid-based delivery system.

In another aspect, the invention is a tissue engineered construct comprising a mammalian cell transfected with a gene for a growth factor and a biocompatible synthetic matrix. In another aspect, the invention is a method for facilitating regeneration of cartilage. The method comprising transfecting a chondrocyte with a gene for a growth factor, seeding the chondrocyte onto a biocompatible synthetic matrix, and implanting the cell-seeded matrix into an in vivo site. The synthetic matrix may comprise poly (glycolic acid), the growth factor may be insulin-like growth factor I, and transfection may be accomplished without a viral vector, for example, with a lipid-based delivery system.

In another aspect, the invention is a transfection vector for a mammalian cell, including a gene for a growth factor. The cell may be a chondrocyte, a hepatocyte, Islet cell, nerve cell, muscle cell, bone-forming cell, fibroblast, endothelial cell, stem cell, connective tissue stem cell, mesodermal stem cell, or epithelial cell. The growth factor may be a protein, for example, TGF-β, TGF-α, acidic fibroblast growth factor, basic fibroblast growth factor, epidermal growth factor, IGF-I and II, vascular endothelial-derived growth factor, bone morphogenetic proteins, hepatocyte, platelet-derived growth factor, heparin binding growth factor, hematopoetic growth factor, or peptide growth factor. The gene may include human IGF-I expression vector pCMVhIGF-I. The gene may comprise an active fragment that is 50%, 75% or 90% homologous to the complete gene for IGF(I). The transfected gene may code for a portion of normal IGF-I that is 50%, 75% or 90% homologous to complete IGF-I.

In another aspect, the invention is a plurality of transfected cells comprising chondrocytes. The chondrocytes are transfected with a gene for a protein, the protein may be a growth factor, for example, insulin-like growth factor I. The cells may be transfected with a vector pCMVhIGF-I.

BRIEF DESCRIPTION OF THE DRAWING

The file of this patent contains at least one drawing executed in color. Copies of this patent with color drawings will be provided by the Office upon request and payment of the necessary fee.

The invention is described with reference to the several figures of the drawing, in which.

DETAILED DESCRIPTION

The invention employs a tissue engineered construct incorporating cells that have been transfected with a particular growth factor or regulator. The invention also includes a tissue engineering method wherein transfected cells are seeded on a synthetic, biodegradable matrix and implanted into a tissue site.

The invention can be practiced with a wide variety of cells. Matrices incorporating cells from a variety of tissues have been exploited in tissue engineering applications and can be employed for use with the present invention. For example, chondrocytes have been seeded on type-II collagen matrices, poly(lactic acid), poly(glycolic acid), PLA-PGA, or other matrices. Hepatocytes, islet cells, nerve cells, muscle cells, other organ cells, bone or cartilage forming cells, other connective tissue cells such as epithelial and endothelial cells, and stem cells such as connective tissue stem cells and mesodermal stem cells may also be seeded on matrices for use with the invention. One skilled in the art will recognize that tissue engineering techniques may be applied to a myriad of hard and soft tissues including metabolic tissue (e.g., liver or pancreas), connective tissue (e.g., skin, bone), and nerve.

For therapeutic applications, it is preferable to practice the invention with mammalian cells, and more preferably human cells. Preferably, the cells are HLA matched with the patient, and, most preferably, the patient's own cells are harvested, transfected, and used to seed the matrices of the invention. The cells may be obtained from cell line culture, biopsy, tissue banks, or other sources known to those skilled in the art.

These cells may be seeded on a wide variety of biocompatible matrices. Preferably, the matrix is also biodegradable. Suitable biodegradable matrices are well known in the art and include collagen-GAG, collagen, fibrin, PLA, PGA, and PLA-PGA co-polymers. Additional biodegradable materials include poly(anhydrides), poly(hydroxy acids), poly(ortho esters), poly(propylfumerates), poly(caprolactones), polyamides, polyamino acids, polyacetals, biodegradable polycyanoacrylates, biodegradable polyurethanes and polysaccharides. Non-biodegradable polymers may also be used as well. For example, polypyrrole, polyanilines, polythiophene, and derivatives thereof are useful electrically conductive polymers that can provide additional stimulation to seeded cells beyond the regulators synthesized by the transfected DNA. Other non-biodegradable, yet biocompatible polymers include polystyrene, polyesters, non-biodegradable polyurethanes, polyureas, poly(ethylene vinyl acetate), polypropylene, polymethacrylate, polyethylene, polycarbonates, and poly(ethylene oxide). Those skilled in the art will recognize that this is an exemplary, not a comprehensive, list of polymers appropriate for tissue engineering applications.

It is preferred that the matrix be formed with a microstructure similar to that of the extracellular matrix that is being replaced. Mechanical forces imposed on the matrix by the surrounding tissue will influence the cells on the artificial matrix and promote the regeneration of extracellular matrix with the proper microstructure. The cross-link density of the matrix may also be regulated to control both the mechanical properties of the matrix and the degradation rate (for degradable scaffolds). The shape and size of the final implant should be adapted for the wound site and tissue type.

PLA, PGA and PLA/PGA copolymers are particularly useful for forming the biodegradable matrices. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. PGA is the homopolymer of glycolic acid (hydroxyacetic acid). In the conversion of glycolic acid to poly (glycolic acid), glycolic acid is initially reacted with itself to form the cyclic ester glycolide, which in the presence of heat and a catalyst is converted to a high molecular weight linear-chain polymer. The erosion of the polyester matrix is related to the molecular weights. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. For example, poly(lactide-co-glycolide) (50: 50) degrades in about six weeks following implantation.

Any biocompatible polymer is suitable so long as it may be formed into a matrix having the necessary porosity for cell viability. The porosity should be such that nutrients can migrate to the cells and waste products can diffuse away from the cells. The pores should also be large enough for the residence of the cells themselves. The pore size is typically in the range of 50–300 μm and, as noted above, it may be varied within this range to control cell behavior and matrix properties (see U.S. Pat. No. 6,123,727 to Vacanti, et al., the entire contents of which are incorporated herein by reference). Furthermore, within the range of pore size that promotes proper cell metabolism, the size and arrangement of the pores may be controlled to promote a specific timetable and amount of vascular ingrowth from the surrounding tissue as well as migration of native cells and the diffusion of nutrients.

The matrix material may be coated with materials that promote specific adhesion and metabolic behavior of both transfected cells and native cells, using techniques well known in the art. For example, integrins or other cell adhesion molecules may be attached to the matrix. Cell attachment may also be enhanced by coating the matrix with materials such as basement membrane components (e.g., laminin, fibronectin), agar, agarose, collagens types I, II, III, or IV, glycosaminoglycans, polyvinyl alcohol, and other hydrophilic materials and mixtures thereof. Alternatively, amino acids such as lysine or poly(lysine) may be coated onto the matrix. Regulators or growth factors such as TGF-β may also be attached to the matrix to promote specific metabolic activity. Other bioactive molecules that may be attached to the matrix or incorporated into the matrix during cell seeding include growth factors such as fibroblast growth factor, epidermal growth factor, or various morphogenic factors known to those skilled in the art. Such bioactive molecules are well known in the art and are commercially available or described in both the tissue engineering and endocrinology literature. An effective dosage of a given growth factor or regulator for a given cell may be determined experimentally in vitro by determining a dosage that increases cell proliferation, metabolism, or survival as compared with untreated controls. In addition, an anti-inflammatory agent may be used to decrease inflammation in the implanted matrix, decreasing the growth of scar-like tissue into the matrix.

The cell may be transfected with a nucleic acid encoding specific regulators and cytokines. Other molecules, genes, or nucleic acids that influence cell growth, matrix production, or other cellular functions such as cell cycle may also be used. Nucleic acids may be DNA, RNA, or other nucleotide polymers. Such polymers may include natural nucleosides, nucleoside analogs, chemically modified bases, biologically modified bases, intercalated bases, modified sugars, or modified phosphate groups. The growth factors encoded may include those described above and others that are well known to those skilled in the art. For example, fibroblasts may be transfected with TGF-β. As noted above, chondrocyte metabolism is increased by IGF-I, and muscle cells have been successfully transfected with genes for therapeutic proteins (Powell, 1999). Other exemplary growth factors include epidermal growth factor, bone morphogenetic protein, vascular endothelial-derived growth factor, hepatocyte growth factor, platelet-derived growth factor, TGFα, IGF-II, hematopoetic growth factors, heparin binding growth factor, peptide growth factors, and basic and acidic fibroblast growth factors. In some embodiments it may be desirable to incorporate genes for factors such as nerve growth factor (NGF) or muscle morphogenic factor (MMP). The particular growth factor employed should be appropriate to the desired cell activity. The regulatory effects of a large family of growth factors are well known to those skilled in the art.

Vectors containing the transfected gene may be any of those known in the art. The gene may be transfected into a cell using a linear piece of nucleic acid, a circular plasmid, a ss-nucleic acid, a ds-nucleic acid, a virus, a YAC, etc. The complete gene for the growth factor may be transfected, or active fragments of the gene that are 50, 75, or 90% homologous to the complete gene may be used. The transfected gene may code for the entire growth factor protein, for a peptide including a portion of the protein, or for portions of the protein that are 50, 75, or 90% homologous to the growth factor.

A variety of gene transfection techniques are known in the art. For example, viral vectors such as adenovirus are commonly used to insert DNA into a variety of cells. Other transfection methods include electroporation, Ca-phosphate methods, and lipid based methods. A wide variety of techniques are well known in the art (Sambrook et al., *Molecular Cloning: A Laboratory Manual,* 2nd Ed., 1989; Miller and Calos, eds., Gene Transfer Vectors for Mammalian Cells, 1987; Ausubel et al., eds., *Current Protocols in Molecular Biology,* 1987; each of which is incorporated herein by reference). Both stable transfection and transient expression techniques may be employed, depending on how long the growth factor should be expressed. For example, a growth factor promoting a wound healing response need only be produced for a few days, while it may be desirable to express a gene for a factor regulating metabolic activity for a longer period of time.

The gene encoding the growth factor to be expressed may be operably linked to other elements regulating expression of the gene, including, but not limited to, a promoter, an enhancer sequence, repressor sequence, TATA box, transcription stop sequence, ribosomal binding site, etc. One of skill in the art would appreciate the variety of elements that may be used in combination with the growth factor gene. These growth factor genes may also be transfected with an appropriate promoter, such as a cytomegalovirus promoter operably linked to the growth factor cDNA to be transcribed. In general, appropriate promoters should be selected for the cell type being transfected. In addition, the growth factors may be transfected with appropriate enhancer or repressor regions to further control expression of the growth factor gene being transfected. Effective enhancers and repressors for a variety of cells are well known to those skilled in the art. The genes may also be co-transfected with ribosomal binding sites or transcription stop and start sites to enhance the transcription of the growth factor gene. The DNA sequence may also include flanking regions to facilitate incorporation of the genetic material into the chromosomes of the transfected cells.

EXAMPLES

Methods

Cells were transfected as described in Gene Therapy (Madry, 2000, the contents of which are incorporated herein by reference). Reagents were obtained from GIBCO Life Technologies (Grand Island, N.Y., USA) unless otherwise indicated. FUGENE 6™ (Boehringer Mannheim, Mannheim, Germany) is a non-liposomal mixture of lipids. Bovine testicular hyaluronidase was from Sigma (St. Louis, Mo., USA), Plasticware was from Falcon (Becton Dickinson Labware, Franklin Lakes, N.J., USA).

A human IGF-I cDNA (Jansen, et al. (1983) "Sequence of cDNA encoding human insulin-like growth factor I precursor." *Nature* 306: 609–11) from the plasmid pBShIGF-I containing the entire coding region was inserted as a 760 bp PstI fragment into pcDNA3.1/Zeo(+) (Invitrogen, Carlsbad, Calif.) containing the human cytomegalovirus immediate-early promoter/enhancer and the bovine growth hormone polyadenylation signal. The plasmid was designated pCMVhIGF-I. For the expression of β-galactosidase, the vector pCMVSportβGal (Gibco Life Technologies, Grand Island, N.Y.) containing the *E. coli* lacZ gene under the control of the CMV-IE promoter/enhancer was used. Plasmids were subjected to endotoxin-free maxipreparation (Qiagen, Hilden, Germany).

Bovine articular cartilage was obtained from radiocarpal joints of 1 to 2-week old calves; the underlying vascularized cartilage was discarded. Harvested cartilage was washed, diced into 2×2 mm pieces and transferred to DMEM with 100 U/mL penicillin G, 50 mg/mL ascorbic acid, and 100 μL/ml streptomycin (basal medium) containing collagenase at 37° C. in a humidified atmosphere with 5% $CO_2$ for 16 h. Isolated cells were filtered through at 125 μm mesh to remove undigested matrix. Bovine chondrocytes were isolated with 0.08–0.09% collagenase. Cell number was determined by hemocytometry. Viability, as determined by trypan blue exclusion, always exceeded 90%. Isolated chondrocytes were placed in monolayer culture in 24-well plates at a density of $6×10^4$ cells per well in basal medium containing 10% fetal bovine serum (growth medium).

The cells were cultured for 3–4 days without passage until subconfluent (60–70% density) and divided into three groups. Group one served as a mock-transfected control. Group two was transfected with an *E. coli* β-galactosidase (lacZ) gene as a marker gene. Group three was the experimental group and was transfected with a human IGF-I expression vector pCMVhIGF-I using the FUGENE 6™ delivery system, as described below. For overexpression of human IGF-I (hIGF-I), the previously characterized expression plasmid vector pCMVhIGF-I that contains a hIGF-I cDNA (Jansen, 1983) under control of the human cytomegalovirus immediate-early promoter/enhancer (CMV-IE) and the bovine growth hormone polyadenylation signal was used (Madry, et al., unpublished data).

The eukaryotic expression vector pCMVSportβGal containing the *E. coli* lacZ gene under the control of the cytomegalovirus immediately-early promoter and enhancer was propagated in DH5α competent cells. Ultrapure endotoxin-free plasmid DNA was prepared using the Quiagen Endofree Plasmid Maxi Kit according to the manufacturer's instructions. The chondrocyte monolayer was rinsed once with Opti-MEM. For transfections, non-liposomal lipid/DNA complexes were prepared according to the manufacturer's instructions in sterile polypropylene tubes and added to the chondrocytes. Cells were incubated at 37° C. for 4 h, washed with DMEM and incubated for a further 48 h with growth medium. The optimal (v/w) transfection (lipid)/DNA ratio is 3:1 for the bovine articular chondrocytes described above. The optimal quantity of DNA is 1 μg, and transfection efficiency is increased significantly by exposure to 4U/mL hyaluronidase both 12 hours before transfection and during transfection (Madry, 2000). Similar transfection conditions also produce excellent results in human articular chondrocytes; however, a lipid-DNA ratio of 2:1 is preferred for osteoarthritic human chondrocytes.

Bovine articular chondrocytes transfected with pCMVhIGF-I secrete 83±22 ng IGF-I per 1×10$^7$ cells/24h that is biologically active (Madry, et al, unpublished data). For the expression of β-galactosidase, the vector pCMVSportβGal containing the *E. coli* lacZ gene under the control of the CMV-IE promoter/enhancer was applied. One day after transfection, cells were dissociated from the culture plates and dynamically seeded (5×10$^6$ cells/scaffold) in a non-woven polyglycolic (PGA) mesh (Freed, et al.(1994) "Biodegradable polymer scaffolds for tissue engineering", *Biotechnology* 12:689–693) (5 mm diameter ×2 mm thick disks) in basal medium supplemented with 10% calf serum. The mean cell viability after seeding was 95.2±3.4%, 94.8±1.2 % and 94.9±2.4 % for constructs based on pCMVSportβGal-transfected, pCMVhIGF-I-transfected, or normal chondrocytes, respectively (n=3, P>0.05). After 2 days, constructs were transferred to rotating bioreactors (Synthecon, Houston, Tex.) (Freed, et al. (1998) "Chondrogenesis in a cell-polymer-bioreactor system." *Exp. Cell Res.* 240: 58–65) and cultured freely suspended for up to 38 days post transfection. Constructs were sampled at day 10, 21, 28 and 38 post transfection.

Samples for gene expression were assayed for β-galactosidase activity by X-gal staining (Madry, 2000). Briefly, constructs were fixed for 10 min in 10% formalin and stained for 4 h at 37° C. for β-galactosidase (In-situ β-galactosidase Staining Kit, Stratagene). For histology and immunohistochemistry, constructs were fixed for 24 h in 10% formalin. Paraffin-embedded sections (5 μm) were stained with safranin O. For type-I and type-II collagen immunostaining, sections were deparaffinized in xylene, passed through decreasing concentrations of ethanol, washed in PBS and submerged for 30 min in 0.3% hydrogen peroxide. After washing with PBS, sections were incubated for 30 min in 33 U/mL bovine testicular hyaluronidase (Sigma), washed with PBS and further incubated 30 min. in 10% horse serum in PBS (blocking buffer). Sections then were incubated with a 1:100 dilution of a monoclonal anti-bovine type-I collagen IgG (Sigma), a 1:20 dilution of an anti-bovine type-II collagen IgG (Developmental Studies Hybridoma Bank, Ames, Iowa, USA) or a 1:20 dilution of a monoclonal aggrecan (Serotec, Oxford, UK) in blocking buffer for 45 min. at room temperature. The primary antibody was detected by the Vectastain Elite ABC kit (Vector Laboratories, Burlingame, Calif., USA) using diaminobenzidine as the chromogen. Positive controls included bovine articular cartilage with vascular structures (collagens type I and II, aggrecan) and rat skin (collagen type I). Negative controls included samples without the primary antibody, rat skin (type II and aggrecan) and bovine articular cartilage (type I collagen).

Morphometric measurements of the diameter of the cartilaginous constructs were performed standardized at the horizontal and vertical axis of a safranin-O stained horizontal section by image analysis using Adobe Photoshop 5.0 (Adobe Systems, Mountain View, Calif.).

Samples for biochemical analysis were lyophilized and digested for 16 h at 56° C. with 1 mg/mL proteinase-K (Sigma) solution in 50 mM Tris, 1 mM EDTA, 1 mM iodoacetamide with use of 1 mL of enzyme solution per 4–10 mg dry weight of the sample. The DNA content of the constructs was assessed by the Hoechst 33258 assay using a QM- 1 spectrofluorometer (Photon Technology International, South Brunswick, N.J.) (Kim, et al. (1988) "Fluorometric assay of DNA in cartilage explants using Hoechst 33258."*Anal. Biochem.* 174: 168–76). The glycosaminoglycan content of the constructs was determined spectrophotometrically (Perkin-Elmer, Norwalk, Conn.) with the use of dimethylmethylene blue (Serva, Darmstadt, Germany) (Farndale, et al. (1986) "Improved quantification of sulphated glycosaminoglycans by use of dimethylmethylene blue." *Biochim. Biophys. Acta* 883: 173–77). Total collagen content was determined from the measured hydroxyproline content after acid hydrolysis in 6N HCl at 115° C. for 18 h and reaction with p-dimethylaminobenzaldehyde and choramine-T with the use of a hydroxyproline/collagen ratio of 1:10 (Woessner, et al. (1961) "The determination of hydroxyproline in tissue and protein samples containing small proportions of this imino acid." *Arch. Biochem. Biophys.* 93: 440–47). Collagen and proteoglycan synthesis rates were determined by measuring the incorporation of [$^3$H] proline and [35S] sulfate (NEN, Boston, Mass.), respectively as previously described (Freed, 1998).

To determine IGF-I protein production, engineered constructs (n=2 per experiment) were individually incubated in 1 mL basal medium for 24 h at ten days post transfection. This conditioned medium or medium removed from the bioreactor was subjected to a three-step acid acid-ethanol extraction of binding proteins. The IGF-I content was determined by radioimmunoassay (detection limit: 20 ng/mL; Nichols Institute, San Juan Capistrano, Calif.) in 1 mL conditioned medium as described above or in the regular bioreactor culture medium in which the constructs were cultured.

For mechanical evaluation, engineered constructs were equilibrated for 1 h at room temperature in 0.15 M phosphate buffered saline (PBS, pH 7.4) supplemented with 100 U/mL penicillin, 100 μg/mL streptomycin, and protease inhibitors, and cored into disks (3 mm diameter, 2 mm thickness). Samples were mounted in an electrically insulating cylindrical confining chamber as previously described (Frank, et al. (1987) "Cartilage electromechanics—II. A continuum model of cartilage electrokinetics and correlation with experiments." *J. Biomech.* 20: 629—39). The chamber was mounted in a servo-controlled Dynastat mechanical spectrometer (Imass, Hingham, Mass.), and the specimen was compressed between a porous polyethylene platen and an Ag/AgCl electrode, with an identical electrode placed in the surrounding bath. Pre-implantation samples were compressed at initial 10% strain and then sequential increments of 5% up to a maximum of 35%. Post-implantation samples were compressed at initial 5% strain and then sequential increments of 2% up to a maximum of 15%. After stress relaxation, the equilibrium stress was measured and plotted against the applied strain; the equilibrium modulus was determined from the slope of the best linear regression fit (Frank, 1987).

The protocol for in vivo implantation used was approved by the Animal Care and Use Committee at the Massachusetts Institute of Technology. Six constructs per group were sampled from bioreactors 28 days post transfection, implanted in dorsal subcutaneous pouches in immunocompromised mice (NIH Swiss Nude; 25–30 g, Charles River, Cambridge, Mass.), harvested after 10 more days and assayed for reporter gene expression, histological appearance and biomechanical properties.

Data are expressed as mean ±SD. Four independent experiments were performed with 10–12 constructs per condition for bioreactor studies. Differences between groups were compared using two-way analysis of variance (ANOVA). A two-tailed P<0.05 was considered statistically significant.

Results—Structural Properties

Figure 1:
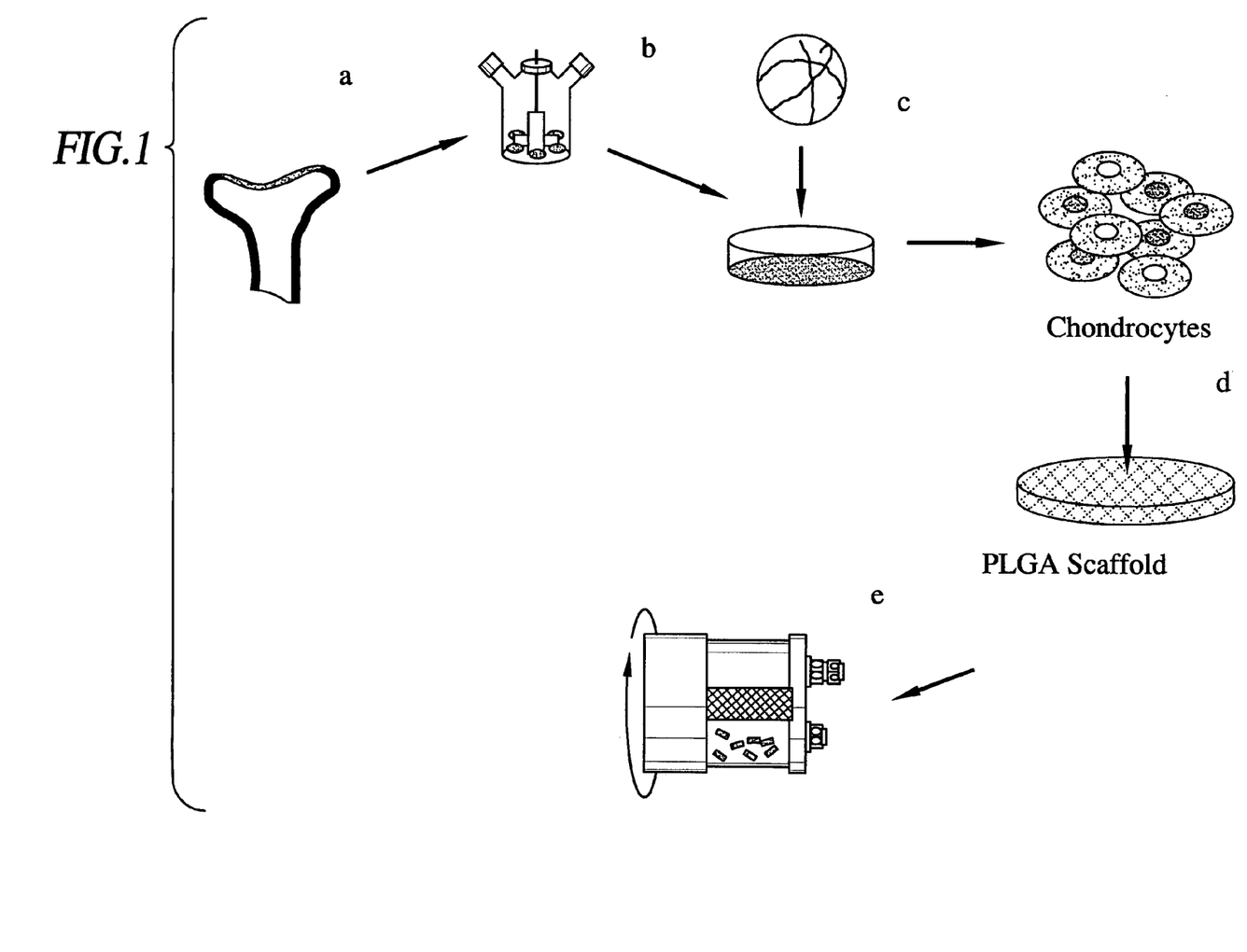
FIG. 1 is a schematic showing the transfection and seeding method used in the invention.
Figure 2A:
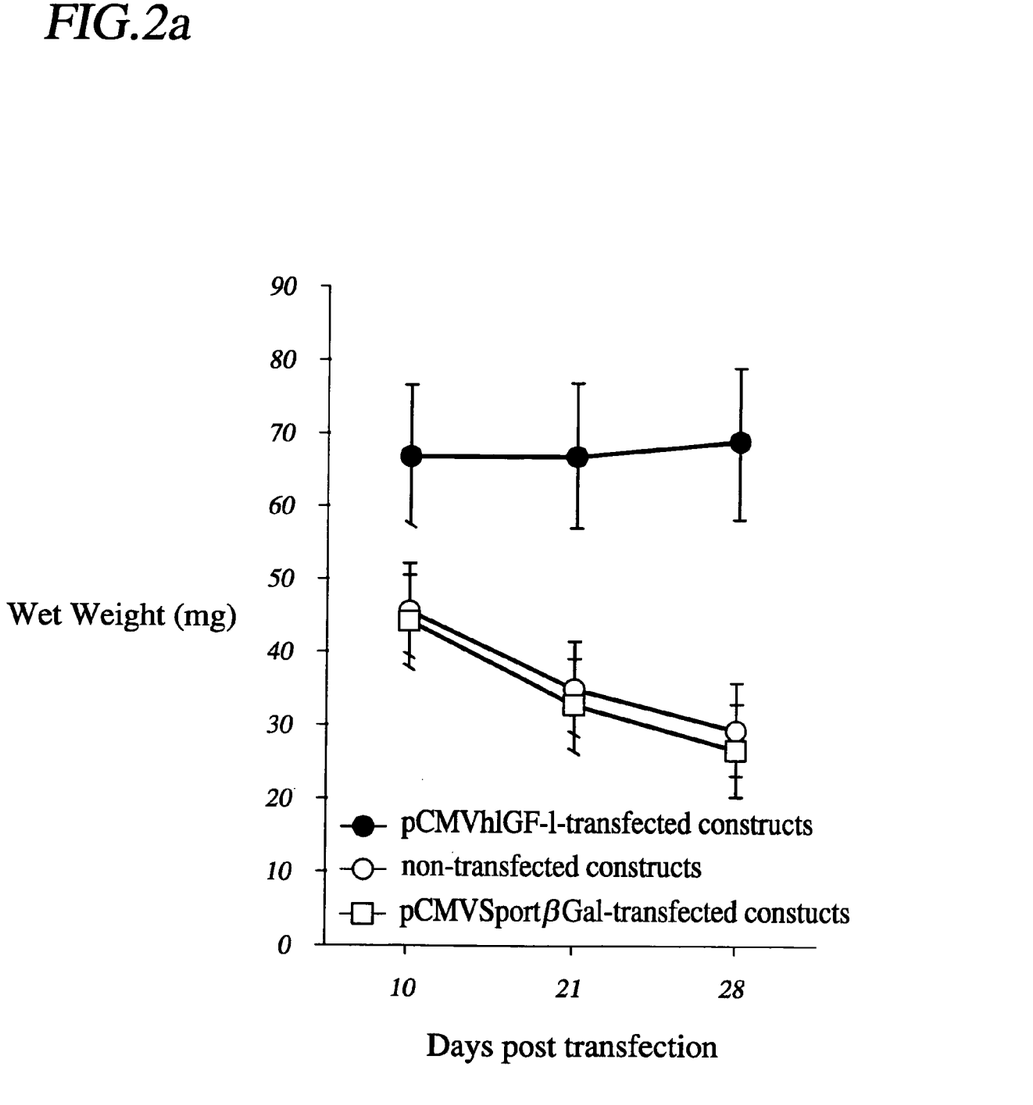
FIG. 2A is a graph depicting the wet weight of engineered constructs seeded with chondrocytes transfected with ((○) lacZ expression plasmid vector pCMVSportβGAL, (•) the human IGF-I expression plasmid vector pCMVhIGF-I, or (□) non-transfected chondrocytes at 10, 21, and 28 days post-transfection (n=10)
Figure 2B:
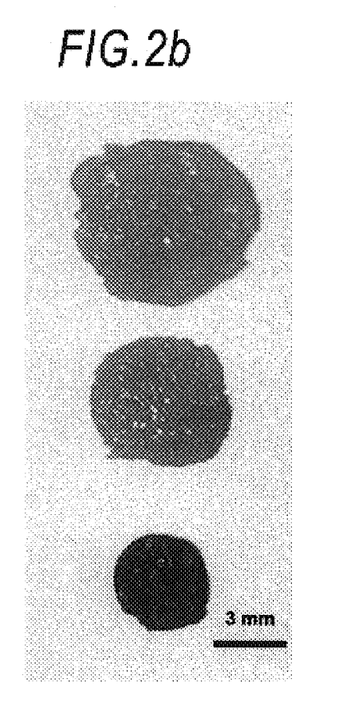
FIG. 2B is light micrographs of cross-sections of experimental and control constructs that were stained in toto with x-gal 28 days post-transfection (top: IGF-I group, middle: non-transfected group, bottom: lacZ-transfected group)
Figure 2C:
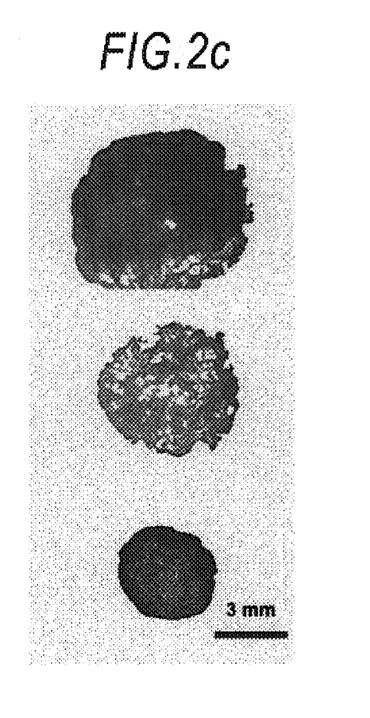
FIG. 2C includes light micrographs of experimental and control constructs that were stained in toto with safrinin O 28 days post-transfection (top: IGF-I group, middle: non-transfected group, bottom: lacz-transfected group)

Constructs based on pCMVhIGF-I-transfected chondrocytes maintained their wet weight over the period of bioreactor cultivation, while the wet weights of constructs from non-transfected and pCMVSportβGal-transfected chondrocytes decreased over time (FIG. 2). After 28 days of cultivation, the weight and the mean diameter of pCMVhIGF-I-transfected constructs were significantly higher than those of non-transfected or pCMVSportβGal-transfected constructs (Tables 1 and 2).* based on pCMVhIGF-I-transfected chondrocytes had a DNA content 1.5-fold higher than that of pCMVSportβGal-transfected constructs and 1.9-fold higher than that of constructs based on normal chondrocytes (Table 1). The glycosaminoglycan content in constructs based on pCMVhIGF-I-transfected chondrocytes was 11.1-fold higher than in constructs based on pCMVSportβGal-transfected chondrocytes and 8-fold higher than in constructs based on normal chondrocytes. The total collagen content in constructs based on pCMVhIGF-I-transfected chondrocytes was 2.0-fold

TABLE 1

| | Genetically modified constructs | | |
|---|---|---|---|
| Parameter | pCMVSportβGal | pCMVhIGF-I | Normal constructs |
| Construct structure | | | |
| Weight (mg wet) | 26.5 ± 2.1 | 67.7 ± 10.8 | 29.0 ± 8.5 |
| | (n = 10, P < 0.001) | (n = 10) | (n = 10, P < 0.001) |
| Weight (mg dry) | 2.2 ± 0.4 | 5.8 ± 1.1 | 2.8 ± 0.4 |
| | (n = 10, P < 0.001) | (n = 10) | (n = 10, P < 0.001) |
| Diameter (mm) | 5.6 ± 0.1 | 6.5 ± 0.2 | 5.3 ± 0.2 |
| | (n = 10, P < 0.001) | (n = 10) | (n = 10, P < 0.001) |
| Water (%) | 92.5 ± 1.0 | 91.3 ± 0.9 | 88.7 ± 3.5 |
| | (n = 6, P > 0.05) | (n = 5) | (n = 6, P > 0.05) |
| DNA | 97.5 ± 13.9 | 148.6 ± 23.1 | 76.8 ± 14.0 |
| (ng per construct) | (n = 6, P = 0.001) | (n = 5) | (n = 6, P = 0.001) |
| GAG | 96.3 ± 15.3 | 1068.6 ± 239.6 | 133.3 ± 51.1 |
| (μg per construct) | (n = 6, P = 0.001) | (n = 5) | (n = 6, P < 0.001) |
| GAG | 1.0 ± 0.1 | 7.1 ± 0.6 | 1.7 ± 0.4 |
| (μg per ng DNA) | (n = 6, P < 0.001) | (n = 5) | (n = 6, P < 0.001) |
| Collagen | 0.6 ± 0.1 | 1.3 ± 0.2 | 0.5 ± 0.1 |
| (mg per construct) | (n = 6, P < 0.001) | (n = 2) | (n = 6, P < 0.001) |
| Collagen | 5.8 ± 0.7 | 8.5 ± 0.5 | 7.1 ± 1.0 |
| (g per ng DNA) | (n = 6, P < 0.001) | (n = 5) | (n = 6, P = 0.015) |

*Structural and functional parameters of engineered constructs based on pCMVSportβGal-, pCMVhIGF-I-transfected or normal chondrocytes. All parameters were assessed at day 28 post transfection. Data represent mean ± standard deviation. Statistical significance was assessed using ANOVA. Parentheses indicate the number of samples analyzed per group followed by the P value for comparing the respective control group with constructs based on pCMVhIGF-I-transfected chondrocytes.

TABLE 2

| | Genetically modified constructs | | |
|---|---|---|---|
| Parameter | pCMVSportβGal | pCMVhIGF-I | Normal constructs |
| Chondrocyte function | | | |
| Glucose in medium | 322.0 ± 7.1 | 221.0 ± 52.3 | 311.5 ± 20.5 |
| (mg/dl) | (n = 2, P > 0.05) | (n = 2) | (n = 2, P > 0.05) |
| Lactate in medium | 99.8 ± 7.4 | 180.5 ± 48.8 | 103.5 ± 12.0 |
| (mg/dl) | (n = 2, P > 0.05) | (n = 2) | (n = 2, P > 0.05) |
| [$^3$H] Proline incorporation | 19.5 ± 4.1 | 22.7 ± 3.1 | 21.8 ± 3.6 |
| ($10^3$ cpm/ng DNA/16 h) | (n = 6, P > 0.05) | (n = 5) | (n = 6, P > 0.05) |
| [$^{35}$S] Sulfate incorporation | 1.2 ± 0.3 | 4.7 ± 0.5 | 1.9 ± 0.5 |
| ($10^3$ cpm/ng DNA/16 h) | (n = 6, P < 0.001) | (n = 5) | (n = 6, P < 0.001) |

Figure 3A:
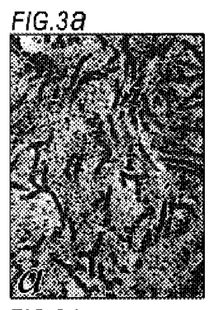
FIGS. 3A, B, C, D, E, F, G, H, I, K, L, and M are horizontal sections of experimental and control constructs seeded with articular chondrocytes 28 days post-transfection with (A, D, G, K) lacZ expression vector pCMVSportβGal, (B, E, H, L) the human IGF-I expression vector pCMVhIGF-I, or (C, F, I, M) non-transfected chondrocytes (stains: A–C: Safraoin O, D–F: a monoclonal anti-type I collagen antibody, G–I: a polyclonal anti-type II collagen antibody, K–M: monoclonal aggrecan antibody).
Figure 3B:
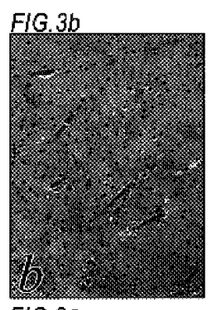
Figure 3C:
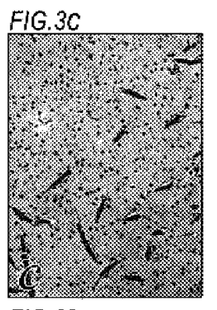
Figure 3D:
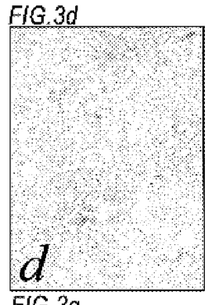
Figure 3E:
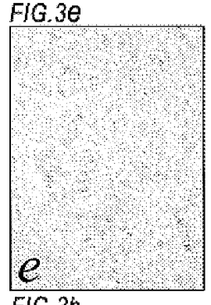
Figure 3F:
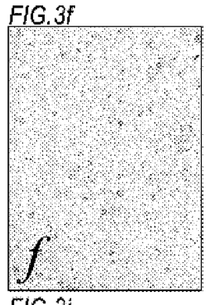
Figure 3G:
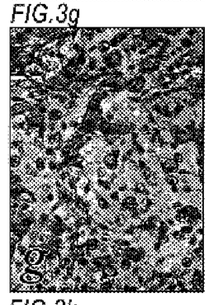
Figure 3H:
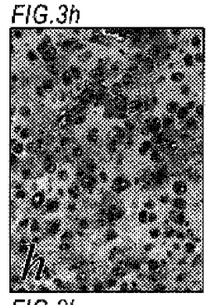
Figure 3I:
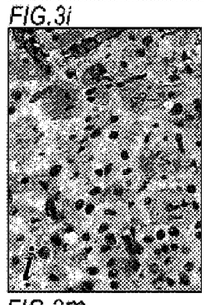
Figure 3K:
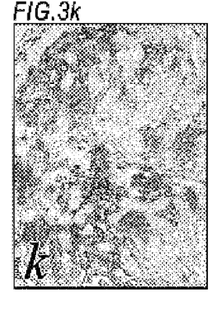
Figure 3L:
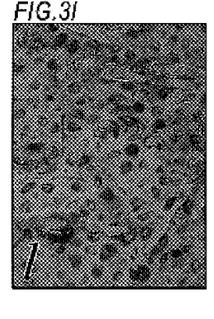
Figure 3M:
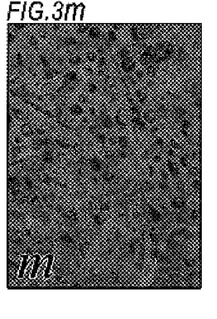

At all time points, constructs incorporating pCMVhIGF-I-transfected chondrocytes appeared histologically more cartilaginous than those in the two control groups, as evidenced by the morphology of chondrocytes and the intensity of safranin O staining (FIG. 2C, 3A–C). After 28 days, immunohistological evaluation demonstrated the absence of type I collagen (FIG. 3D–F) and the presence of type II collagen (FIG. 3G–I) and aggrecan (FIG. 3K–M) in constructs in all groups. In constructs based on pCMVSportβGal-transfected chondrocytes, X-gal-positive cells were found scattered throughout the construct until day 38 post-transfection, the endpoint of this study. Constructs higher than in constructs based on pCMVSportβGal-transfected chondrocytes and 2.4-fold higher than in constructs based on normal chondrocytes. The glycosaminoglycan content per ng DNA in constructs based on pCMVhIGF-I-transfected chondrocytes was 7.1-fold higher than in constructs based on pCMVSportβGal-transfected chondrocytes and 4.2-fold higher than in constructs based on normal chondrocytes. The collagen content per ng DNA in constructs based on pCMVhIGF-I-transfected chondrocytes was 1.5-fold higher than in constructs based on pCMVSportβGal-transfected chondrocytes and 1.2-fold higher than in constructs based on normal chondrocytes.

Human IGF-I was not detected in the bioreactor culture medium or in conditioned medium from individually incubated engineered constructs.

Results—Functional Parameters

Macromolecular incorporation of [$^3$H] proline in constructs based on pCMVhIGF-I-transfected chondrocytes was not significantly different from constructs based on pCMVSportβGal-transfected or normal chondrocytes (Table 1). The equilibrium modulus after 4 weeks in the pCMVhIGF-I-transfected group was 125.0±52.0, 4-fold higher than in the combined control groups (31.5±1.5, n=4, P=0.028).

Results—In vivo Gene Expression

Four-week constructs implanted subcutaneously in mice continued to develop into mature cartilaginous tissue. After 10 days in vivo, constructs were surrounded with a thin fibrous capsule. Constructs based on pCMVSportβGal-transfected chondrocytes had equilibrium moduli of 35+/−33 kPa (n=3). The pCMVhIGF-I-transfected constructs had moduli of 126+/−52 kPa (n=4), and the non-transfected constructs had equilibrium moduli of 30+/−4 kPa (n=3). The pCMVhIGF-I-transfected constructs had significantly higher equilibrium moduli than either control. Gene expression, as determined by X-gal staining of constructs based on pCMVSportβGal-transfected chondrocytes persisted throughout the implantation period that ended on day 38 post transfection.

Discussion

Transfer of a human IGF-I cDNA into primary articular chondrocytes improved the structural and functional properties of bioengineered cartilaginous constructs. These results are consistent with previously reported data on the effects of IGF-I on isolated articular chondrocytes (Trippel, et al. (1989) "Effect of somatomedin-C/insulin-like growth factor I and growth hormone on cultured growth plate and articular chondrocytes." Pediatr. Res. 25: 76–82). Transgene expression was maintained for up to 38 days post transfection in vitro and in vivo, and the resulting constructs were structurally cartilaginous and mechanically functional.

The protocol for each transfection utilized a very short time in monolayer culture and no passaging of the chondrocytes, thereby avoiding phenotypic drift of the chondrocytes (von der Mark, et al. (1977) "Relationship between cell shape and type of collagen synthesis as chondrocytes lose their cartilage phenotype in culture." Nature 267: 531–2). Both pCMVSportβGal- and pCMVhIGF-I-transfected chondrocytes remained viable after dissociation from the cell culture vessel, indicating that neither the transfection procedure applied or nor the transgene products had adverse effect on chondrocyte viability.

Application of pCMVhIGF-I-transfected chondrocytes resulted in a faster rate of chondrogenesis in vitro. In constructs incorporating pCMVhIGF-I-transfected chondrocytes, the amount of collagen, glycosaminoglycan and chondroitin sulfate per ng DNA was significantly higher than in constructs from the two control groups. This suggests that the higher amounts of these macromolecules, in particular collagen, per construct are not secondary to an increase in cell number per construct, but rather reflect an augmented synthesis rate of these molecules by chondrocytes within the construct. These findings are consistent with the role of IGF-I in articular chondrocyte growth and matrix synthesis (Trippel, et al. (1995) "Growth factor actions on articular cartilage." J. Rheumatol. Suppl. 43: 129–32) and in articular cartilage repair (Nixon, 1999).

Constructs incorporating pCMVhIGF-I-transfected chondrocytes exhibited an increase in biosynthetic activity as measured by enhanced [35S] sulfate incorporation, an index for glycosaminoglycan synthesis. Incorporation of [$^3$H] proline, an index for collagen synthesis, remained unchanged between the groups. Their equilibrium modulus, an intrinsic biomechanical parameter that reflects the ability to resist loading, was 4-fold higher as compared to the control constructs but remained subnormal after 10 days of in vivo cultivation. As previously shown, several months are necessary to obtain mechanical properties similar to that of native articular cartilage (Freed, 1997). Constructs from all groups continued to develop in vivo, were mechanically functional following explanation, and maintained transgene expression.

The long availability of the plasmid DNA vector within component chondrocytes is likely to provide maximal benefit for the stimulation of chondrogenesis over a prolonged period of time. In a possible clinical application, the strong CMV-IE promoter/enhancer can be replaced with regulative elements that are tissue-specific or responsive to physiological conditions (Kitamura, et al. (1997) "Creation of an in vivo cytosensor using engineered messangial cells. Automatic sensing of glomerular inflammation controls transgene activity." J. Clin. Invest. 100: 1394–9). Exemplary elements include a type II collagen or aggrecan promoter.

Of interest was the observation that the release of IGF-I from the cartilaginous construct into the culture medium could not be detected. In contrast, in previous experiments, we found significant levels of bioactive human IGF-I following transfection of bovine articular chondrocytes with FuGENE 6 (Madry, et al., unpublished data). Recent data using adenoviral transduction of rabbit articular chondrocytes confirmed the capability of articular chondrocytes to synthesize and secrete bioactive human IGF-I (Smith 2000). It is possible that the IGF-I produced in the experimental constructs was bound to IGF-I binding proteins produced by chondrocytes within the cartilaginous construct (Olney, et al.(1993) "Production and hormonal regulation of insulin-like growth factor binding proteins in bovine chondrocytes." Endocrinology 133: 563–70). The effect of IGF-I appears to be limited to the cartilaginous construct by mechanisms that need to be further elucidated.

Tissue-engineered human bioartificial muscle composed of retroviral modified cells has been previously shown to express and to secrete pharmacologically relevant levels of recombinant human growth hormone (Vandenburgh, et al. (1996) "Tissue-engineered skeletal muscle organoids for reversible gene therapy." Hum. Gene Ther. 7: 2195–200; Powell, 1999). A sustained release of DNA in vivo was achieved when plasmid DNA was associated with a biodegradable carrier (Bonadio, 1999). Although the secretion of bioactive human IGF-I by keratinocytes (Eming, et al. (1996) "Targeted expression of insulin-like growth factor to human keratinocytes: modification of the autocrine control of keratinocyte proliferation." J. Invest. Dermatol. 107: 113–20), differentiated muscle fibers (Alila, et al. (1997) "Expression of biologically active human insulin-like growth factor-I following intramuscular injection of a formulated plasmid in rats." Hum. Gene Ther. 8:1785–95; Barton-Davis, et al. (1998) "Viral mediated expression of insulin-like growth factor I blocks the aging-related loss of skeletal muscle function." Proc. Natl. Acad. Sci. USA 95:15603–7), or chondrocytes (Smith, 2000) has been reported, there have been no previous reports about the use of genetically modified cells for tissue engineering of cartilage.

In summary, this is the first time cells expressing an exogenous growth factor gene have utilized for the tissue engineering of cartilage. The application of gene delivery to the tissue engineering of cartilage resulted in enhanced structural and functional properties of engineered constructs. The characteristics of this system present an unique opportunity to evaluate the effect of different growth factors in a suitable model of chondrogenesis, e.g. by applying tissue—specific promoters such as the type II collagen or aggrecan promoters, using different cells as a source, or for applications different than articular cartilage repair.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of assembling a tissue engineered articular cartilage construct, comprising:
   transfecting a plurality of chondrocytes with a gene for insulin-like growth factor I (IGF-I); and
   seeding the transfected cells onto a biocompatible matrix comprising poly(glycolic acid),
   wherein at least a portion of the transfected cells synthesize collagen type II.

2. The method of claim 1, further comprising culturing the chondrocytes until they synthesize a desired amount of extracellular matrix.

3. The method of claim 1, wherein the matrix further comprises one or more of a synthetic material and a non-synthetic material.

4. The method of claim 3, wherein the matrix further comprises one or more of poly(glycolic acid), collagen-glycosaminoglycan, collagen, poly(lactic acid), poly(lactic-co-glycolic acid), poly(anhydride), poly(hydroxy acid), poly(orthoester), poly(propylfumerate), polysaccharide, polypyrrole, polyaniline, polythiophene, polystyrene, polyester, polyurethane, polyurea, poly(ethylene vinyl acetate), polypropylene, polymethacrylate, polyethylene, poly(ethylene oxide), and poly(carbonate).

5. The method of claim 1, wherein the matrix further comprises one or more of integrins, cell adhesion molecules, cell adhesion sequences, basement membrane components, laminin, fibronectin, agar, agarose, collagen, glycosaminoglycans, poly(vinyl alcohol), amino acids, and polymers of amino acids.

6. The method of claim 1, further comprising adding a cell metabolism regulator to the matrix.

7. A tissue engineered construct, comprising:
   a plurality of chondrocytes transfected with a gene for IGF-I, and
   a biocompatible matrix comprising poly(glycolic acid),
   wherein the construct is characterized by synthesis of collagen type II.

8. The construct of claim 7, wherein the matrix further comprises one or more of a synthetic material and a non-synthetic material.

9. The construct of claim 8, wherein the matrix further comprises one or more of poly(glycolic acid), collagen-glycosaminoglycan, collagen, poly(lactic acid), poly(lactic-co-glycolic acid), poly(anhydride), poly(hydroxy acid), poly(orthoester), poly(propylfumerate), polysaccharide, polypyrrole, polyaniline, polythiophene, polystyrene, polyester, polyurethane, polyurea, poly(ethylene vinyl acetate), polypropylene, polymethacrylate, polyethylene, poly(ethylene oxide), and poly(carbonate).

10. The construct of claim 7, wherein the matrix further comprises one or more of integrins, cell adhesion molecules, cell adhesion sequences, basement membrane components, laminin, fibronectin, agar, agarose, collagen, glycosaminoglycans, poly(vinyl alcohol), amino acids, and polymers of amino acids.

11. The construct of claim 7, further comprising cell metabolism regulator.

* * * * *